United States Patent
Hong et al.

(10) Patent No.: US 10,634,605 B2
(45) Date of Patent: Apr. 28, 2020

(54) METHOD FOR PREDICTING PHYSICAL PROPERTIES OF POLYMERS

(71) Applicant: LG Chem, Ltd., Seoul (KR)

(72) Inventors: Yoon Ki Hong, Daejeon (KR); Hyuck Ju Kwon, Daejeon (KR); Eun Kyoung Song, Daejeon (KR); Dae Sik Hong, Daejeon (KR); Ye Jin Lee, Daejeon (KR); Joong Soo Kim, Daejeon (KR); Eun Young Shin, Daejeon (KR); Young Suk You, Daejeon (KR); Ki Soo Lee, Daejeon (KR)

(73) Assignee: LG Chem, Ltd. (KR)

( * ) Notice: Subject to any disclaimer, the term of this patent is extended or adjusted under 35 U.S.C. 154(b) by 104 days.

(21) Appl. No.: 15/773,663

(22) PCT Filed: Oct. 12, 2017

(86) PCT No.: PCT/KR2017/011256
§ 371 (c)(1),
(2) Date: May 4, 2018

(87) PCT Pub. No.: WO2018/097477
PCT Pub. Date: May 31, 2018

(65) Prior Publication Data
US 2019/0064051 A1    Feb. 28, 2019

(30) Foreign Application Priority Data
Nov. 24, 2016 (KR) .......................... 10-2016-0157723

(51) Int. Cl.
*G01N 17/00* (2006.01)
*G01N 33/44* (2006.01)
*B29C 49/00* (2006.01)
*G01N 30/88* (2006.01)

(52) U.S. Cl.
CPC ............. *G01N 17/00* (2013.01); *B29C 49/00* (2013.01); *G01N 33/442* (2013.01); *C08F 2500/13* (2013.01); *G01N 2030/885* (2013.01)

(58) Field of Classification Search
CPC ................. G01N 17/00; G01N 33/442; G01N 2203/0071; G01N 2203/0069
(Continued)

(56) References Cited

U.S. PATENT DOCUMENTS 7,317,054 B2    1/2008 Starita
9,187,627 B2    11/2015 Mehta
(Continued)

FOREIGN PATENT DOCUMENTS

CN    101679540 A    3/2010
EP    2878623 A1    6/2015
(Continued)

OTHER PUBLICATIONS

Fleißner, M., "Slow Crack Growth and Creep Rupture Strength of Polyethylene Pipe; A laboratory method for quality control", Translated from Kunststoffe German Plastics 77, 1987.
(Continued)

*Primary Examiner* — Nimeshkumar D Patel
*Assistant Examiner* — Jean F Morello
(74) *Attorney, Agent, or Firm* — Lerner, David, Littenberg, Krumholz & Mentlik, LLP

(57) ABSTRACT

The present invention relates to a method for predicting the physical properties of polymers. More specifically, the present invention relates to a method for predicting long-term stability of polymers using a molecular weight distribution curve.

7 Claims, 1 Drawing Sheet

(58) Field of Classification Search
USPC .......................................................... 73/866
See application file for complete search history.

(56) References Cited

U.S. PATENT DOCUMENTS

| | | | |
|---|---|---|---|
| 2002/0123848 | A1 | 9/2002 | Schneiderman et al. |
| 2010/0121006 | A1 | 5/2010 | Cho et al. |
| 2011/0035193 | A1 | 2/2011 | Deslauriers et al. |
| 2012/0316311 | A1 | 12/2012 | Yang et al. |
| 2012/0325515 | A1 | 12/2012 | Steffl et al. |
| 2013/0018154 | A1 | 1/2013 | Buryak et al. |
| 2015/0259455 | A1 | 9/2015 | Hlavinka et al. |
| 2016/0297907 | A1 | 10/2016 | Goode et al. |
| 2016/0333172 | A1 | 11/2016 | Koch et al. |
| 2019/0086308 | A1* | 3/2019 | Lee .................. C08F 10/02 |

FOREIGN PATENT DOCUMENTS

| | | |
|---|---|---|
| EP | 3141566 A1 | 3/2017 |
| JP | 2004514902 A | 5/2004 |
| KR | 20120123675 A | 11/2012 |
| KR | 20140033083 A | 3/2014 |
| KR | 20160010351 A | 1/2016 |
| KR | 101645062 B1 | 8/2016 |
| KR | 20160106660 A | 9/2016 |
| WO | 2008002969 A2 | 1/2008 |

OTHER PUBLICATIONS

Frank, A. et al., "Prediction of the remaining lifetime of polyethylene pipes after up to 30 years in use", Polymer Testing, 2009, 28, p. 737-745.

Hansen, C. M. et al., "Prediction of Environmental Stress Cracking in Plastics with Hansen Solubility Parameters", Ind. Eng. Chem. Res., 2001, 40, p. 21-25.

International Search Report for Application No. PCT/KR2017/011256 dated Jan. 18, 2018.

Lu, X. et al., "The Critical Molecular Weight for Resisting Slow Crack Growth in a Polyethylene", Journal of Polymer Science, Part A Polymer Physics, Jul. 30, 1996, 34(10), p. 1809-1813.

Maxwell, A. S. et al., "Prediction of Environmental Stress Cracking Resistance in Linear Low Density Polyethylenes", Polymer Engineering and Science, 2008, 48(2) p. 360-364.

Shebani, A.N., "The correlation of the molecular structure of polyolefins with environmental stress cracking resistance", University of Stellenbosch, Dec. 2006.

Extended European Search Report and Written Opinion for Application No. EP 17861202 dated Feb. 12, 2019.

Mohammad Javad Shirkavand et al: "Effect of Molecular Structure Parameters on Crystallinity and Environmental Stress Cracking Resistance of High-Density Polyethylene/Ti0 2 Nanocomposites", Advances in Polymer Technology, vol. 37, No. 3, 21719, Received May 6, 2016, pp. 1-8.

Pouyan Sardashti et al: "Improvement of Hardening Stiffness Test as an Indicator of Environmental Stress Cracking Resistance of Polyethylene", Journal of Macromolecular Science, Part A, vol. 49, No. 9, Aug. 6, 2012 (Aug. 6, 2012), pp. 689-698.

Chinese Search Report for Application No. CN 201780004035.4 dated Aug. 16, 2019, 2 pages.

* cited by examiner

METHOD FOR PREDICTING PHYSICAL PROPERTIES OF POLYMERS

CROSS-REFERENCE TO RELATED APPLICATIONS

The present application is a national phase entry under 35 U.S.C. § 371 of International Application No. PCT/KR2017/011256 filed Oct. 12, 2017, which claims priority from Korean Patent Application No. 10-2016-0157723 filed Nov. 24, 2016, all of which are incorporated herein by reference.

BACKGROUND OF THE INVENTION

(a) Field of the Invention

The present invention relates to a method for predicting physical properties of polymers. More specifically, the present invention relates to a method for predicting long-term stability of polymers using a molecular weight distribution curve.

(b) Description of the Related Art

Polyolefin resins used for large-diameter high-pressure pipe tubes generally require high pressure resistance characteristic and excellent processability. The high pressure resistance characteristic is generally a physical property that can be expressed in a high density region, and this is because the higher the degree of crystallization in the polyolefin resin, the modulus increases and thus the strength to withstand high pressure increases.

However, generally, pipes has to assure a long-term pressure resistance stability for at least 50 years, but there is a disadvantage that, if the density is high, the resistance against the brittle fracture mode is deteriorated and the long-term pressure resistance characteristic is deteriorated. In addition, when the molecular weight is low or the molecular weight distribution is narrow, the large diameter pipe is difficult to process due to the occurrence of sagging phenomenon during processing. Consequently, the polyolefin resin having a high molecular weight and a very broad molecular weight distribution should be applied to solve these problems. Especially, if the molecular weight is high, extrusion load is largely generated and pipe appearance is poor, and thus a very wide molecular weight distribution is necessarily required.

Although many attempts have been conducted to improve these problems, there is a problem that the physical properties and processability of the product are not satisfied at the same time. Therefore, manufacture of a superior product having a balance between long-term stability and processability is constantly required.

On the other hand, the long-term pressure resistance stability of the polyolefin resin can be evaluated by a full notch creep test (FNCT). The FNCT requires a long time for measurement, and the measurement error is large. Thus, it is difficult to evaluate the long-term stability of the polyolefin resin within a short period of time, which is a hurdle to the development of a new resin for high-pressure pipes.

SUMMARY OF THE INVENTION

The present invention has been made in view of the above problems, and it is an object of the present invention to provide a method capable of evaluating physical properties of polymers requiring long-term measurement time, associated with the long-term pressure resistance stability among the physical properties of polymers, by using a molecular weight distribution curve of polymers with high reliability within a short period of time.

In order to achieve the above problems, the present invention provides a method for predicting physical properties of polymers comprising the steps of:

measuring a molecular weight distribution curve of the polymer to be measured (herein, a log value of a molecular weight MW (log MW) is denoted by x-axis, and a molecular weight distribution to a log value (dwt/dlog MW) is denoted by y-axis) using a gel permeation chromatography (GPC) at a temperature of 160° C.;

dividing the section between 3.0 and 7.0 on the x-axis of the molecular weight distribution curve into four equal parts to obtain the integral value of the molecular weight distribution curve at each section; and predicting the environmental stress cracking resistance (unit: time) measured by the full notch creep test (FNCT) under the conditions of 6.0 MPa and 80° C. from the integral value.

According to the present invention, there may be provided a method capable of evaluating physical properties of polymers requiring long-term measurement time, associated with the long-term pressure resistance stability among the physical properties of polymers, by using a molecular weight distribution curve of polymers with high reliability within a short period of time.

DETAILED DESCRIPTION OF THE EMBODIMENTS

Figure 1:
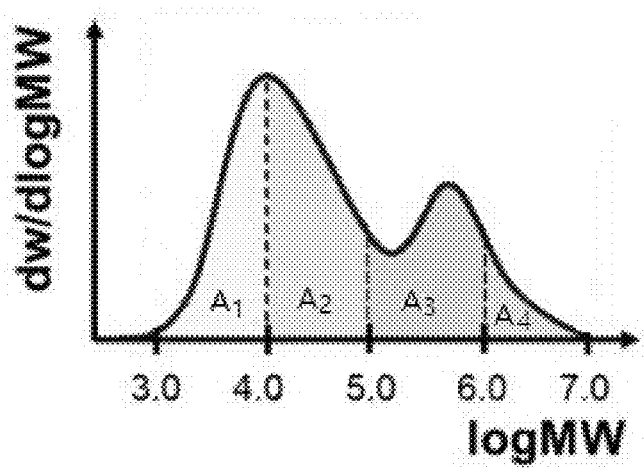
FIG. 1 is a molecular weight distribution curve (GPO curve) measured to predict the physical properties of polymers according to an embodiment of the present invention.

In the present invention, the terms such as "first", "second", etc. are used to describe various components, and the terms are used only for the purpose of distinguishing one component from another.

Moreover, the terminology used herein is for the purpose of describing exemplary embodiments only and is not intended to limit the present invention. Further, singular expressions "a", "an", and "the" used herein may include plural expressions unless the context clearly indicates otherwise. In addition, it should be understood that the meaning of the term "comprising", "including", "having" and the like is intended to specify the presence of stated features, numbers, steps, components or combinations thereof and does not exclude existence or addition of one or more other features, numbers, components or combinations thereof.

The invention can make various modifications and take various forms, and thus specific embodiments are illustrated and described in detail below. It should be understood, however, that the invention is not intended to be limited to any particular disclosure form, but includes all modifications, equivalents and alternatives falling within the spirit and scope of the invention.

Hereinafter, a method for predicting the physical properties of polymers according to specific embodiments of the invention will be described.

According to one embodiment of the present invention, there is provided a method for predicting physical properties of polymers comprising the steps of:

measuring a molecular weight distribution curve of the polymer to be measured (herein, a log value of a molecular weight MW (log MW) is denoted by x-axis, and a molecular weight distribution to a log value (dwt/dlog MW) is denoted by y-axis) using a gel permeation chromatography (GPC) at a temperature of 160° C.; and dividing the section between 3.0 and 7.0 on the x-axis of the molecular weight distribution curve into four equal parts to obtain the integral value of the molecular weight distribution curve at each section; and predicting the environmental stress cracking resistance (unit: time) measured by the full notch creep test (FNCT) under the conditions of 6.0 MPa and 80° C. from the integral value.

According to one embodiment of the present invention, the environmental stress cracking resistance can be predicted according to the following Equation 1 for the integral value:

Environmental stress cracking resistance=
$(-271)*A_1+(-318)*A_2+(-459)*A_3+155*A_4+29,586$     [Equation 1]

in Equation 1 above, $A_1$ is an integral value of a molecular weight distribution curve in the section where log MW is 3.0 to 4.0, $A_2$ is an integral value of a molecular weight distribution curve in the section where log MW is 4.0 to 5.0, $A_3$ is an integral value of a molecular weight distribution curve in the section where log MW is 5.0 to 6.0, $A_4$ is an integral value of a molecular weight distribution curve in the section where log MW is 6.0 to 7.0, and the integral value of $A_1$ to $A_4$ means relative values when the integral value of the entire molecular weight distribution curve is 100.

In the present invention, the polymer to be measured may be a polyolefin. Also, the polyolefin may be a polymer or a copolymer obtained by polymerizing one or more monomers selected from the group consisting of ethylene, propylene, 1-butene, 1-pentene, 1-hexene, 4-methyl-1-pentene, 1-octene, 1-decene, 1-dodecene, 1-tetradecene, 1-hexadecene, 1-octadecene, and eicosene.

The polyolefin is a resin obtained by polymerizing an olefin-based monomer such as ethylene in the presence of a catalyst such as metallocene, and is used in various fields due to excellent physical properties.

The physical properties of the polyolefin can be evaluated in several respects. For example, the weight average molecular weight, the number average molecular weight, the molecular weight distribution, the melt flow rate (MFR), the melt flow rate ratio (MFRR), the density, Full Notch Creep Test (FNCT) and the like can be measured and used comprehensively for evaluating the physical characteristics such as strength, processability and stability of polymers.

Among them, a polyolefin resin used in a pressure-resistant heating pipe, a large-diameter high-pressure pipe, or the like is required to have long-term stability under high pressure conditions. In order to evaluate such long-term stability, Notch pipe test (NPT) is performed at Exova. Sweden according to ISO 13479 and is widely adopted as a standardized evaluation method.

However, there is a problem that Notch pipe test (NPT) takes more than one year and the time and cost are consumed excessively, and thus the full notch creep test (FNCT) which is a simplified method is largely used as a method for evaluating a long-term stability of the high pressure pipe.

FNCT is a method according to ISO 16770 which is described in detail in M. Fleissner in Kunststoffe 77 (1987), pp. 45 et seq. However, since the measurement of the FNCT takes more than about one month and the measurement error is relatively large, it is difficult to evaluate and analyze the long-term stability of polymer resins.

Thus, the present inventors have conduced continuous research about a method for evaluating the long-term stability of polymer resins, and found that there is a certain correlation between the integral value for each section of the molecular weight distribution curve (GPC curve) of the polymer resin and the FNCT, thereby developing a method for predicting FNCT from the molecular weight distribution curve with a high reliability within a short period of time. The present invention has been completed on the basis of such finding.

That is, it was confirmed that, through measurement of the molecular weight distribution of a polymer resin, particularly a polyolefin resin, the long-term stability could be predicted beforehand in products manufactured using the polymer resin. For example, it can be usefully used for a method for predicting FNCT of a polyolefin resin having a high molecular weight and high molecular weight distribution (PDI) in which the weight average molecular weight is 100,000 to 1,000,000 g/mol, or 100,000 to 800,000 g/mol, or 100,000 to 500,000 g/mol and the molecular weight distribution is 5 to 30, or 10 to 30, or 15 to 30.

The environmental stress cracking resistance predicted according to Equation 1 above may be a value according to the time (hr) measured at 6.0 MPa and at 80° C. with a full notch creep test (FNCT) according to ISO 16770.

Hereinafter, a method for predicting physical properties of polymers according to an embodiment of the present invention will be described with reference to the drawings.

FIG. 1 is a molecular weight distribution curve (GPO curve) measured to predict the physical properties of polymers according to an embodiment of the present invention.

First, the molecular weight distribution curve (GPO curve) is obtained for the polymer to be measured at 160° C. using a gel permeation chromatography (GPO). The log value (log MW) of the molecular weight (MW) is denoted by x-axis, and the molecular weight distribution (dwt/dlog MW) to the log value is denoted by y-axis.

In the x-axis of the molecular weight distribution curve, that is, the log value of the molecular weight (log MW), the section between 3.0 and 7.0 is divided into four equal parts to obtain the integral values of molecular weight distribution curves in each section.

In the above molecular weight distribution curve, when the log MW includes a section deviating from 3.0 to 7.0, the deviating section is excluded, and only the section between 3.0 and 7.0 is divided into four equal parts to obtain the integral value.

Meanwhile, the method for predicting the physical properties of polymers according to the present invention may have a higher reliability when the sum of the integral values $(A_1+A_2+A_3+A_4)$ in a section where log MW is 3.0 to 7.0 is close to 100 in the molecular weight distribution curve.

Referring to FIG. 1, the integral value $A_1$ of the molecular weight distribution curve in the section where log MW (x-axis) is 3.0 to 4.0 is obtained. Similarly, the integral value $A_2$ of the molecular weight distribution curve in the section between 4.0 and 5.0, the integral value $A_3$ of the molecular weight distribution curve in the section between 5.0 and 6.0, and the integrated value $A_4$ of the molecular weight distribution curve in the section between 6.0 and 7.0 can be obtained from the GPC curve, respectively. In this case, the integral value of $A_1$ to $A_4$ is used as a relative value when the integral value of the entire molecular weight distribution curve is 100.

The present inventors have conducted a regression analysis by comparing the relative values for each section ($A_1$, $A_2$, $A_3$, $A_4$) obtained from GPC curve for the various polymer resins as described above, especially the polyolefin resin, with the actual measurement value of the FNCT, and as a result derived a relational equation below between the integral value for each section and the environmental stress cracking resistance measured by the full notch creep test (FNCT) under the conditions of 6.0 MPa and 80° C.

Environmental stress cracking resistance=
$(-271)*A_1+(-318)*A_2+(-459)*A_3+155*A_4+$
29,586                [Equation 1]

in Equation 1 above, $A_1$ is an integral value of a molecular weight distribution curve in the section where log MW is 3.0 to 4.0 and $A_2$ is an integral value of a molecular weight distribution curve in the section where log MW is 4.0 to 5.0, $A_3$ is an integral value of a molecular weight distribution curve in the section where log MW is 5.0 to 6.0, and $A_4$ is an integral value of a molecular weight distribution curve in the section where log MW is 6.0 to 7.0.

The environmental stress cracking resistance according to Equation 1 is a physical property according to the time (hr) measured at 6.0 MPa and at 80° C. with a full notch creep test (FNCT) according to ISO 16770.

As a result of verifying We above Equation 1 for a large number of polyolefin resins prepared by various preparation methods, it was found that the relationship between the environmental stress cracking resistance predicted or calculated according to Equation 1 and the time measured with a full notch creep test (FNCT) measured at 6.0 MPa and 80° C. according to ISO 16770 is 0.8 or more, or 0.9 or more, which is highly reliable.

From the above relational equation, the FNCT requiring a long time measurement from the GPC curve, which is relatively easy to measure, can be obtained with high reliability, and it is expected that the cost and time required for evaluating the long-term stability can be greatly reduced. In particular, FNCT can be predicted for a newly developed polymer resin within a short period of time, and it is expected that it will contribute greatly to the research and development of a new resin.

Hereinafter, the present invention will be described in more detail by way of examples. However, these examples are presented for illustrative purposes only and the scope of the invention is not limited thereto in any way.

EXAMPLES

Examples 1 to 6

Six types of polyethylene resins having various molecular weight distribution curves and having a density in the range of 0.930 to 0.950 g/cm$^3$ were prepared by polymerizing ethylene according to the established method by a metallocene catalyst.

From the molecular weight distribution curve of each polyethylene, the environmental stress cracking resistance of the polyethylene resin was calculated by the following Equation 1.

Environmental stress cracking resistance=
$(-271)*A_1+(-318)*A_2+(-459)*A_3+155*A_4+$
29,586                [Equation 1]

in Equation 1 above, $A_1$ is an integral value of a molecular weight distribution curve in the section where log MW is 3.0 to 4.0 and $A_2$ is an integral value of a molecular weight distribution curve in the section where log MW is 4.0 to 5.0, $A_3$ is an integral value of a molecular weight distribution curve in the section where log MW is 5.0 to 6.0, and $A_4$ is an integral value of a molecular weight distribution curve in the section where log MW is 6.0 to 7.0, and the integral value of $A_1$ to $A_4$ means relative values when the integral value of the entire molecular weight distribution curve is 100.

In addition, the actual measurement value of FNCT, which is the time (hr) measured by the full notch creep test (FNCT) according to ISO 16770 at 6.0 MPa and 80° C., and the environmental stress cracking resistance (hr) according to Equation 1 are compared, and the results are shown in Table 1 below.

Figure 2:
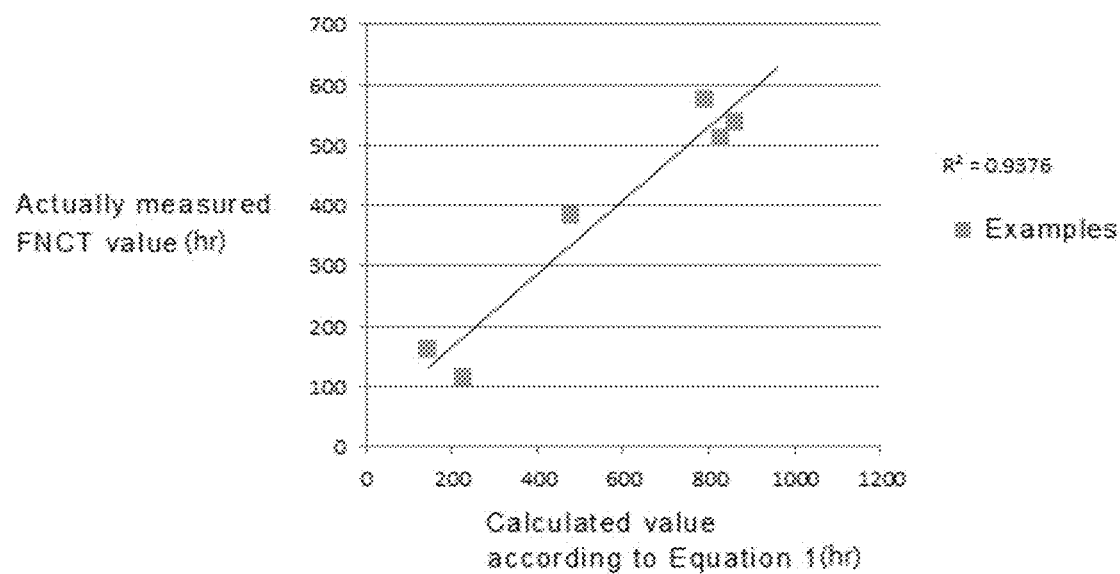
FIG. 2 is a graph showing a relationship between the calculated value of the environmental stress cracking resistance according to Equation 1 and the actual measurement value of FNCT.

The relationship between the calculated value of environmental stress cracking resistance according to Equation 1 and the actual measurement value of FNCT is shown in FIG. 2.

1) Molecular weight distribution curve: Continuous molecular weight distribution was measured using a gel permeation chromatography (GPC) at a measurement temperature of 160° C., and a log value of the molecular weight MW (log MW) was denoted by x-axis, and the molecular weight distribution of log MW (dwt/dlog MW) was denoted by y-axis, to thereby draw a molecular weight distribution curve.

2) Full Notch Creep Test; FNCT was described in M. Fleissner in Kunststoffe 77 (1987), pp. 45 et seq. and measured according to ISO 16770 which has been implemented so far. In ethylene glycol which is a stress crack promoting medium using a tension of 6.0 MPa at 80° C., the breakage time was shortened due to the shortening of the stress start time by a notch (1.6 mm/safety razor blade). The test piece was manufactured by sawing three test pieces with a size of width 10 mm, height 10 mm and length 90 mm from a compressed nameplate having a thickness of 10 mm. A central notch was provided to the test specimen using a safety razor blade in a notch element specifically manufactured for this purpose. The notch depth was 1.6 mm.

TABLE 1

|  | Weight average molecular weight (g/mol) | Molecular weight distribution | Integral value for each section of GPC curve | | | | Equation 1 Calculated value (hr) | FNCT Actual measured value (hr) |
| --- | --- | --- | --- | --- | --- | --- | --- | --- |
|  |  |  | $A_1$ | $A_2$ | $A_3$ | $A_4$ |  |  |
| Example 1 | 282,228 | 21.77 | 16.84771 | 46.21066 | 25.3944 | 10.04293 | 225.9044 | 115 |
| Example 2 | 366,132 | 10.91 | 5.516394 | 55.77089 | 25.85677 | 10.685 | 143.8318 | 161 |
| Example 3 | 318,468 | 27.21 | 23.28312 | 41.87206 | 23.68627 | 8.969476 | 479.2303 | 383 |

TABLE 1-continued

| | Weight average molecular weight (g/mol) | Molecular weight distribution | Integral value for each section of GPC curve | | | | Equation 1 Calculated value (hr) | FNCT Actual measured value (hr) |
|---|---|---|---|---|---|---|---|---|
| | | | $A_1$ | $A_2$ | $A_3$ | $A_4$ | | |
| Example 4 | 327,770 | 25.36 | 20.32166 | 46.56404 | 21.54408 | 9.325724 | 828.2199 | 512 |
| Example 5 | 340,126 | 22.35 | 14.12229 | 50.39516 | 22.78621 | 10.24219 | 861.8676 | 537 |
| Example 6 | 336,559 | 16.45 | 11.11483 | 57.50293 | 19.56069 | 9.555881 | 790.7542 | 576 |

As shown in Table 1 and FIG. 2, the stress crack resistance calculated according to Equation 1 of the present invention showed a highly reliable predictability with $R^2=0.9376$ in comparison with the actually measured FNCT value.

What is claimed is:

1. A method for predicting physical properties of polymers comprising the steps of:

measuring a molecular weight distribution curve of the polymer to be measured (herein, a log value of a molecular weight MW (log MW) is denoted by x-axis, and a molecular weight distribution to a log value (dwt/dlog MW) is denoted by y-axis) using a gel permeation chromatography (GPC) at a temperature of 160° C.;

dividing the section between 3.0 and 7.0 on the x-axis of the molecular weight distribution curve into four equal parts to obtain the integral value of the molecular weight distribution curve at each section; and predicting the environmental stress cracking resistance (unit:time) measured by the full notch creep test (FNCT) under the conditions of 6.0 MPa and 80° C. from the integral value.

2. The method for predicting the physical properties of polymers according to claim 1, wherein the environmental stress cracking resistance is calculated according to the following Equation 1:

Environmental stress cracking resistance=
$(-271)*A_1+(-318)*A_2+(-459)*A_3+155*A_4+29,586$  [Equation 1]

in Equation 1 above, $A_1$ is an integral value of a molecular weight distribution curve in the section where log MW is 3.0 to 4.0, $A_2$ is an integral value of a molecular weight distribution curve in the section where log MW is 4.0 to 5.0, $A_3$ is an integral value of a molecular weight distribution curve in the section where log MW is 5.0 to 6.0, $A_4$ is an integral value of a molecular weight distribution curve in the section where log MW is 6.0 to 7.0, and the integral value of $A_1$ to $A_4$ means relative values when the integral value of the entire molecular weight distribution curve is 100.

3. The method for predicting the physical properties of polymers according to claim 1, wherein the polymer to be measured is a polyolefin.

4. The method for predicting the physical properties of polymers according to claim 3, wherein the polyolefin is a polymer or a copolymer obtained by polymerizing one or more monomers selected from the group consisting of ethylene, propylene, 1-butene, 1-pentene, 1-hexene, 4-methyl-1-pentene, 1-octene, 1-decene, 1-dodecene, 1-tetradecene, 1-hexadecene, 1-octadecene, and eicosene.

5. The method for predicting the physical properties of polymers according to claim 3, wherein the polyolefin has a weight average molecular weight of 100,000 to 1,000,000 g/mol.

6. The method for predicting the physical properties of polymers according to claim 3, wherein the polyolefin has a molecular weight distribution of 5 to 30.

7. The method for predicting the physical properties of polymers according to claim 3, wherein the polyolefin is used for a high-pressure pipe.

* * * * *